United States Patent [19]

Lippard et al.

[11] Patent Number: 4,843,161

[45] Date of Patent: Jun. 27, 1989

[54] PLATINUM-INTERCALATIVE COMPLEXES FOR THE TREATMENT OF CANCER

[75] Inventors: Stephen J. Lippard; Bruce E. Bowler, both of Cambridge, Mass.

[73] Assignee: Massachusetts Institute of Technology, Cambridge, Mass.

[21] Appl. No.: 616,362

[22] Filed: Jun. 1, 1984

[51] Int. Cl.[4] .................... C07F 15/00; A61K 31/555; A61K 31/70; C07H 73/00
[52] U.S. Cl. ........................................ 546/10; 536/6.4
[58] Field of Search ............................................ 546/10

[56] References Cited

U.S. PATENT DOCUMENTS 4,760,156  7/1988  Hefferman .......................... 556/137

Primary Examiner—Mark L. Berch
Attorney, Agent, or Firm—George W. Neuner; Ernest V. Linek

[57] ABSTRACT

Anticancer drug compositions are provided by chemically linking a platinum anticancer drug to an intercalative drug with a linking group that does not inactivate either drug.

7 Claims, No Drawings

PLATINUM-INTERCALATIVE COMPLEXES FOR THE TREATMENT OF CANCER

BACKGROUND OF THE INVENTION

The invention described herein was made in the course of work under a Grant or Award from the National Cancer Institute, Contract No. CA-34992.

This invention relates to novel plantinum-intercalative complexes for the treatment of cancer.

Prior to the present invention, there have been available a wide variety of plantinum compounds useful as antitumor agents. These available platinum antitumor compounds are quite effective against a variety of tumors. However, they have limited solubility in water, which renders their administration to human patients difficult. In addition, it is common to encounter tumor cell lines which are resistant to these therapeutic plantinum compounds, such as cisplatin.

Representative antitumor platinum compounds are disclosed, for example, in U.S. Pat. Nos. 4,053,587; 4,115,418; 4,140,707; 4,177,263; 4,258,051; 4,339,437; and 4,419,351.

In addition, it is well known that intercalative drugs such as vinblastine and bleomycin are effective antitumor drugs. Intercalative compounds are those which insert themselves between the base pairs of the DNA double helix and may bind to specific sites of the nucleotides forming the DNA. By binding in this manner, the intercalative drug is believed to prevent the cellular reproduction of DNA and thereby to inhibit or prevent further growth of the tumor.

It has been proposed by Bagetta et al in Cancer Treatment Reports, Volume 66, No. 6, June 1982, to combine cis-diamminedichloroplatinum (II) (cisplatin) with vinblastine the bleomycin, the latter being an intercalative drug, in order to treat patients afflicted with metastatic malignant melanoma. The authors state that the administration of this combination of drugs appears not to be indicated for general use, due to the cumulative toxicity of cisplatin. It also has been reported by Wittes et al, Oncology, Vol 32, pages 202–207 (1975) that there is a synergism noted when cisplatin and bleomycin are administered to a patient concomitantly for cancer treatment.

It would be highly desirable to provide a means for administering antitumor drugs which affords convenient administration and which is at least as effective in the treatment of cancer as are presently available chemotherapeutic agents. Furthermore, it would be highly desirable to provide such a meanswhich is capable of treating a spectrum of different cancers.

SUMMARY OF THE INVENTION

This invention provides novel anticancer drugs comprising a DNA intercalative drug chemically linked to a platinum anticancer drug in order to form a single molecule which can be administered to a patient. It has been found that the compounds of this invention are more highly water-soluble than the counterpart unmodified platinum drug, and that they are toxic toward tumor cells which are resistant to the unmodified platinum antitumor drug when adminstered alone. The intercalative drug and the platinum anticancer drug are joined together by a molecular bridge which does not adversely affect the activity of either the intercalative drug or the platinum drug against tumor cells. Preferred molecular bridges are an alkyl chain, polyamine chain, polyether chain or the like, which can be of variable length and composition.

DESCRIPTION OF SPECIFIC EMBODIMENTS

The compounds of this invention are formed from a platinum compound having antitumor activity which includes a site to which a linking chain can be attached such as a reactive ring substituent, i.e., an amino group, a hydroxyl group, a sulfhydryl group, a reactive ring carbon, a ring nitrogen group, or the like. The ring nitrogen group is utilized to bind the linking moiety between the intercalative compound and the platinum compound. Representative suitable platinum compounds include dichloroethylenediamineplatinum(II), cis-diamminedichloroplatinum(II), 1,2-diaminocyclohexanedichloroplatinum(II), cis-diamminemalonatoplatinum(II), or the like.

Representative suitable intercalative drugs are those having intercalative activity and having a moiety to which the linking group can be attached, e.g., a ring nitrogen atom. Representative suitable intercalative drugs include acridine orange, 2-methoxy-6-chloro acridine, 9-amino acridine, proflavin or other acridines, adriamycin, daunomycin, ellipticine, ethidium bromide, and related phenanthridines.

The compounds of this invention are prepared in a manner which does not adversely affect the intercalative activity of the intercalative drug or the antitumor activity of the platinum drug. A typical synthesis of a compound of this invention will be described herein, with refernce to acridine orange as the intercalative drug, and dichloroethylenediamine-platinum(II) as the antitumor platinum drug having the formula:

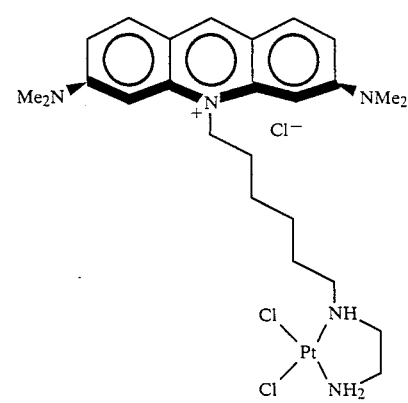

FORMULA I

The starting materials, acridine orange hydrochloride and 6-chloro-1-hydroxyhexane, are reacted under conditions to protect the hydroxyl group of the 6-choro-1-hydroxyhexane with dihydropyran. The choride group is then substituted with iodide, using the Finklestein-Halide exchange reaction, which is carried out with NaI/NaHCO$_3$/acetone. The iodo compound thereby produced then is condensed with the free base form of acridine orange in a suitable solvent such as hot xylene, thereby to cause the quarternization of the ring nitrogen. This reaction yields acridine orange with an alkyl side chain containing a protected hydroxyl group at the end of the chain. The protection of the hydroxyl functionality is effected in dilute acid, such as dilute HCl in ethanol. Thereafter, the hydroxyl group is substituted with bromide utilizing 48% hydrobromic acid to produce the alkylated acridine orange with a reactive bromine at the end of alkyl chain. The bromine is easiy substituted by ethylenediamine in a suitable solvent, such as methanol, thereby to produce an alkylated acridine orange with an ethylenediamine group at the end of the alkyl chain. This compound then is reacted with $PtI_4^{2-}$ in a suitable solvent, such as dimethylformamide and water, thereby to effect attachment of the platinum ion to the ethylenediamine chelate. The two iodides are substituted with chloride by using a stoichiometric amount of silver nitrate followed by treatment with HCl to produce the compound of Formula I.

The compound of Formula I is useful as an antitumor drug and has several advantages over cisplatin. For example, its aqueous solubility is 20 mg/ml, which is far superior to that of cisplatin, 3 mg/ml. In addition, the compound of Formula I also has a much greater ability to unwind DNA than other plantinum altitumor drugs, due to the high intercalative affinity of the acridine orange moiety for DNA. Bot the acridine organe and the platinum moeities are biologically active compounds. Having the two in one molecule enhances the effects of both. It has been found that the compound of Formula I not only is active against normal tumor cells, but it is active against cisplatin-resistance tumor cells. In addition, it has been found that the compound of Formula I is a photoactive DNA degradation agent.

The following examples illustrate the present invention and are not intended to limit the same.

Suitable dosages for utilizing the drugs of this invention comprise between about 25 mg/kg body mass and about 2.5 mg/kg. For example, the compound of Formula I can be utilized at a dosage of between about 2.5 mg/kg and about 15 mg/kg.

EXAMPLE 1

Synthetic Procedures

Protected 6-chlorohexanol (II):

31.0 ml of dihydropyran (341 mmol) was dissolved in 375 ml of $CH_2Cl_2$. 1.36 g of PPTS was added at a catalyst. 26 ml of 6-chlorohexanol (227 mmol) was added and the solution was stirred at room temperature for 5 hours. The mixture was then washed in a separatory funnel with $2 \times 250$ ml of half concentrated NaCl solution with 2 g of $NaHCO_3$ per 250 ml. The $CH_2Cl_2$ phase was dried with anhydrous $Na_2SO_4$. Removal of the solvent by rotary evaporation yielded 49.8 g of a crude yellow material. Vacuum distillation ($<10$ torr) yielded a main fraction of 31.7 g (63%, b.p: 99°-100° C. 10 torr) as a clear liquid.

Protected 6-iodohexanol (III):

All glassware was dried in an oven prior to use. 10 g of II (45.3 mmol) was dissolved in 50 ml of dry distilled acetone. 3.8 g of $NaHCO_3$ (45.4 mmol) was added to the reaction mixture followed by 20.4 g of NaI (136.1 mmol). This mixture was refluxed under $N_2$ for 19 hours. The acetone was removed by rotary evaporation.

The residue was dissolved in deionized $H_2O$. Two layers formed in the separatory funnel. The mixture was extracted with $2 \times 50$ ml of $Et_2O$. The combined ether layers were washed with 50 ml D.I. $H_2O$ ($+\frac{1}{2}$ g $NaHCO_3$) and then dried with $Na_2SO_4$. The solvent was then removed by rotary evaporation and the oil obtained was dried in a vacuum desiccator overnight. Yield: 13.1 g (92.0%).

Quarternized Acridine Orange with a Protected Alcohol:

All glassware was dried in an oven overnight. The xylene was dried over 4 A molecular sieves. The acridine orange free base was dried in a vacuum desiccator overnight. 11.77 g (37.7 mmol) of III and 65 ml of Xylene was mixed together. 5 g (18.8 mmol) of acridine orange was added as a suspension. A spatula tip full of $NAHCO_3$ was added. The mixture was refluxed with vigorous stirring for $5\frac{1}{2}$ hours. The reaction mixture was cooled and suction filtered. After washing with $Et_2O$ a bright orange microcrystalline solid was obtained. After drying in a vacuum desiccator the crude yield was 8.9 g (83.6%). The product was recrystallized twice from EtOH with $Et_2O$ added to the fog point. 7.96 g (73.3%) of a bright red-orange microcrystalline solid was obtained.

Synthesis of Alcohol (VI):

5.36 g (9.61 mmol) of the protected alcohol (V) was dissolved in 300 ml of 95% EtOH by heating on a steam bath. 2.6 ml of concentrated HCl to make a 0.1M HCl/EtOH solution was added. The solution was stirred on a steam bath for 2 hours and then stirred at room temperature for 2 more hours. The solvent was then removed by rotary evaporation producing a deep red solid. The solid was triturated with $Et_2O$ and then dissolved in 250 ml of D.I. $H_2O$. The $H_2O$ solution was washed with $3 \times 50$ ml of $Et_2O$ in a separatory funnel. The water layer was then evaporated by rotary evaporation. The crude yield after drying in a vacuum desiccator was 4.68 g (97.8%). Recrystal lization from 1:1 i-PrOH:MeOH yielded several crops of crystals ranging from dark red needle-like crystals to bright red microcrystalline solids. Total recrystallized yield: 3.34 g (69.8%).

Synthesis of Bromine Compound (VII):

48% HBr was distilled from red phosphorous under $N_2$. 1.3 g (2.63 mmol) of the alcohol VI was added directly to 60 ml of the freshly distilled 48% HBr. The mixture was stirred on an oil bath under $N_2$ at 95° C. for $4\frac{1}{2}$ hours. The solution was then poured into 250 ml of cold D.I. $H_2O$. An immediate light orange precipitate formed. This was collected by suction filtration through a glass frit. This was followed by washing with D.I. $H_2O$ and $Et_2O$. After drying overnight in a vacuum dessicator, 1.3 g (97%) of VII was obtained. This material was found to decompose somewhat during recrystallization from alchohols. Since the crude solid proved to be very pure by $^1H$ NMR it was used without further purification.

Synthesis of Ligand:

The bromine compound (VII) was dried thoroughly in a vacuum desiccator before the reaction. All glassware was oven dried before use. 2.80 g of VII (5.5 mmol) was suspended in 200 ml of dry distilled MeOH. The reaction vessel was flushed with $N_2$ and then 7.36 ml of dry distilled ethylenediamine (110 mmol) was added by syrine. The reaction was stirred at 70° C. under a constant pressure of $N_2$. After the first hour all of VII had completely dissolved. The reaction was stirred $6\frac{1}{2}$ hours total and then most of the MeOH was removed by rotary evaporation. 40 ml of DMF was added and removed at 55° C. by rotary evaporation using a vacuum pump. A deep red brown solid formed in the flask. This was dried in a vacuum desiccator overnight. The solid was triturated with $Et_2O$ ($3 \times 30$ ml) and dried in a vacuum desiccator again. Yield: 3.12 g (quantitative).

Recrystallization of the ligand to Produce the Tetra-HCl Salt:

2 g of the crude ligand was suspended in 100 ml of dry distilled EtOH. This was brought into solution on a steam bath. Dry HCl gas was passed through the solution. A precipitate initially formed, but this redissolved as more HCl was bubbled through, producing a much deeper red solution than originally. The solution was slowly cooled to room temperature covered with a rubber septum and then cooled in an ice bath. The solid formed was collected by suction filtration, washed with cold EtOH (200 proof), and dried on the filter under a fast flow of $N_2$. This yielded 1.6 g (77.3%) of the tetra-HCl salt after drying in a vacuum desiccator.

Platinum Diiodo Complex with Ligand (IX):

A pH 10 solution of 0.5 g (0.848 mmol) of VIII was prepared initially in 10 ml of D.I. $H_2O$. This was concentrated by rotary evaporation after adding 5 ml of DMF. A white solid was removed and a final 15 ml solution of 2:1 DMF:$H_2O$ was prepared. 0.5 g (1.21 mmol) of $K_2PtCl_4$ was dissolved in 5 ml of D.I. $H_2O$. 1.61 g of KI (9.68 mmol) was dissolved in 5 ml of D.I. $H_2O$. The KI solution was added dropwise to the $K_2PtCl_4$ solution over 15 minutes, after which the solution was heated at 50° C. for 15 minutes. Then 20 ml of DMF was added. The ligand solution was added slowly to the $K_2PtI_4$ solution over 2 hours. DMF was added when needed to keep everything in solution. The solution was stirred overnight at 50° C. The solvent volume was then reduced to a low volume by rotary evaporation. D.I. $H_2O$ was added to precipitate the product. This product was filtered, washed with EtOH and $Et_2O$, and then dried on a vacuum desiccator overnight. Yield: 744.7 mg (89.2%) of IX.

Dichloro Platinum Complex X:

300 mg (0.305 mmol) of IX was dissolved in 15 ml of DMF. 153.7 mg (1.06 mmol) of $AgNO_3$ was dissolved in 3 ml of DMF. This latter solution was added dropwise to the solution of IX. A heavy whitish precipitate formed. The solution was heated on a steam bath to coagulate the AgI and then stirred 5 minutes more. The solution was then filtered through a Millipore filter (yield: 203.8 mg 95.9% of AgI), stirred for an additional hour covered with foil and then cooled in a refrigerator at 0° C. for 1 hour. After filtering through a Millipore filter again the solution was concentrated by rotary evaporation to low volume and 5 ml of DMF and 5 ml of 0.4M HCl were added. After sitting overnight the solution was filtered. After removing all but 1–2 ml of DMF by rotary evaporation, the product was precipitated by adding iPrOH. The solid was collected by suction filtration and washed with EtOH and $Et_2O$. After drying in a vacuum desiccator 196.3 mg of X (90.6%) was obtained as a bright red solid.

EXAMPLE II

Toxicity tests were conducted in mice with the compound of Formula I. A series of culture plates with the cell culture set forth in Table I were exposed to varying concentrations of the compounds to determine the concentration at which cell growth rate decreased by 50% ($ID_{50}$). The results are set forth in Table I:

TABLE I

| Cell Line | $ID_{50}$, Mg/ml |
|---|---|
| L1210 (leukemia tumor cell line) | 0.83 |
| T1815 | 3.15 |

TABLE I-continued

| Cell Line | $ID_{50}$, Mg/ml |
|---|---|
| L1210 $\overline{PDD}$ (cis platinum resistant tumor cell line) | 4.16 |

Varying concentrations of the compound of Formula I, i.e., 2.5, 5.0, 10.0, 20.0 and 40.0 mg/kg were each administered to two mice to determine the effect of the compound on the viability of the mice. At 2.5 and 5.0 mg/kg, the mice remained alive. At 10.0 mg/kg, the mice lost weight after 14 days. After 20 and 40 mg/kg, the mice died.

Mice were implanted with the L1210 cell line interperitonally and thereafter some of the mice were administered with doses of the compound of formula I ranging from 6.7 to 20 mg/kg. The optimal dose is 15 mg/kg giving a %ILS of 51% versus control mice implanted with L1210 but not treated with the drug. Results are shown in detail in Table II. %ILS values for cisplatin (cisDDP) are also shown in Table II for comparison.

TABLE II

| Line | Drug | Dose | Schedule | Mean | ILS |
|---|---|---|---|---|---|
| L1210/0 | Formula I | 20 | d 1, 5, 9, 13 | 9.9 | 10% |
| | | 10 | | 12.3 | 38% |
| | | 5 | | 10.6 | 19% |
| | CisDDP | 3 | | 11.9 | 34% |
| L1210/0 | Formula I | 15 | d 1, 5, 9, 13 | 13.9 | 51% |
| | | 10 | | 11.3 | 23% |
| | | 6.7 | | 11.3 | 23% |
| | CisDDP | 4.5 | | 19.6 | 113% |
| | | 3.0 | | 13.9 | 51% |
| | | 2.0 | | 11.6 | 26% |

Treatment with the compound of formula I, of mice implanted with a tumor cell line resistant to cisDDP using doses ranging from 6.7 to 15 mg/kg showed mild activity. These results are shown in Table III.

TABLE III

| Line | Drug | Dose | Schedule | Mean | ILS |
|---|---|---|---|---|---|
| L1210/PDD | Formula I | 15 | q4d × 4 | 12.3 | 12% |
| | | 10 | | 12.1 | 10% |
| | | 6.7 | | 11.4 | 4% |
| | CisDDP | 4.5 | | 11.0 | 0 |
| | | 3.0 | | 10.8 | 0 |
| | | 2.0 | | 11.0 | 0 |

We claim:

1. A platinum-intercalative composition comprising a DNA intercalative compound chemically linked to a platinum antitumor compound, wherein said composition exhibits biological activity attributable to each compound.

2. The composition of claim 1 wherein said DNA intercalative compound is an acridine compound.

3. The composition of claim 1 wherein said acridine compound is acridine orange.

4. The composition of claim 1 wherein said platinum compound is dichloroethylenediamine-platinum(II).

5. The composition of claim 2 wherein said platinum compound is dichloroethylenediamine-platinum(II).

6. The composition of claim 3 wherein said platinum compound is dichloroethylenediamine-platinum(II).

7. The compound of Formula I having the formula:

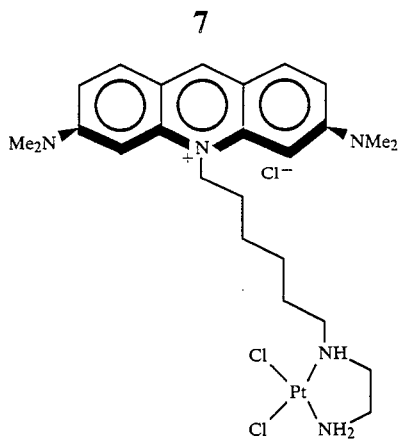
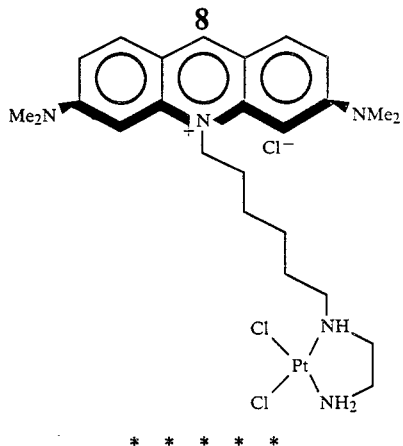
* * * * *